United States Patent [19]

Chasar

[11] 4,439,564
[45] Mar. 27, 1984

[54] 5-MEMBERED CYCLIC PHOSPHONATES AND COMPOSITIONS THEREOF

[75] Inventor: Dwight W. Chasar, Northfield, Ohio
[73] Assignee: The B. F. Goodrich Co., Akron, Ohio
[21] Appl. No.: 427,362
[22] Filed: Sep. 29, 1982
[51] Int. Cl.³ ............................. C07F 9/28; C08K 5/53
[52] U.S. Cl. ................................ 524/101; 252/400 A; 260/936; 524/117
[58] Field of Search ............... 252/400.2, 400.23; 260/936; 524/101, 117

[56] References Cited

U.S. PATENT DOCUMENTS

| | | | |
|---|---|---|---|
| 3,796,684 | 3/1974 | Dever et al. | 524/117 |
| 4,025,486 | 5/1977 | Gilles | 260/936 |
| 4,276,232 | 6/1981 | Rasberger | 524/117 |

*Primary Examiner*—John Kight, III
*Assistant Examiner*—R. A. White
*Attorney, Agent, or Firm*—J. Hughes Powell, Jr.

[57] ABSTRACT

2-[Alkyl substituted-phenoxy]-2,3-dihydro-1,2-benzoxaphosphole 2-oxide, cyclic phosphonates prepared, for example from hindered phenols and ortho-methylolphenols, are effective heat stabilizers and antioxidants for organic materials subject to degradation by heat, oxygen and the like, and result in effective stabilizer systems when combined with hydroxyphenylalkylenyl isocyanurates.

29 Claims, No Drawings

5-MEMBERED CYCLIC PHOSPHONATES AND COMPOSITIONS THEREOF

BACKGROUND OF THE INVENTION

While many cyclic phosphorus-containing chemicals have been proposed and used as stabilizers for a variety of organic materials subject to degradation by heat, oxygen, ultra-violet light, etc., many of them are limited to specific applications, and or have certain deficiencies. For example, tris($\beta$-naphthyl)phosphite has been tested as a stabilizer for vinyl chloride polymers, and has been suggested as a stabilizer for polyamides, but this phosphite has been found to be unsatisfactory as a stabilizer for hydrocarbon polymers. Also, some of the more effective cyclic phosphite stabilizers for poly(olefins) such as distearyl pentaerythitol diphosphite are hydrolytically unstable, both on the shelf and in the polymer. Cyclic phosphorus-containing stabilizers that provide improved heat stability to organic materials subject to degradation, that are less susceptible to hydrolysis, and that form improved combinations with other stabilizers, are desired.

SUMMARY OF THE INVENTION

2-[Alkyl substituted-phenoxy]-2,3-dihydro-1,2-benzoxaphosphole 2-oxide, cyclic phosphonates prepared, for example from hindered phenols and ortho-methylolphenols, are effective heat stabilizers and antioxidants for organic materials subject to degradation by heat, oxygen and the like, and result in effective stabilizer systems when combined with hydroxyphenylalkylenyl isocyanurates.

DETAILED DESCRIPTION

The 2-[alkyl substituted-phenoxy]-2,3-dihydro-1,2-benzoxaphosphole 2-oxides have the following generic formula:

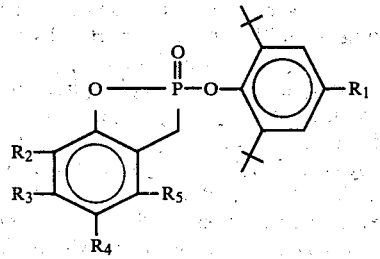

wherein:

$\dagger$ is t-butyl;

$R_1$ is hydrogen, an alkyl radical containing 1 to 8 carbon atoms, a cycloalkyl radical containing 3 to 6 carbon atoms, halogen, an alkoxy radical containing 1 to 8 carbon atoms, phenyl, a —$CH_2CH_2COOR_6$ wherein $R_6$ is an alkyl radical containing 1 to 8 carbon atoms, or t-alkyl radical containing 4 to 8 carbon atoms;

$R_2$ is hydrogen, an alkyl radical containing 1 to 8 carbon atoms, and methoxy or phenyl when $R_3$, $R_4$ and $R_5$ are hydrogen, or when $R_3$ and $R_4$ are hydrogen and $R_5$ is methyl;

$R_3$ is methyl when $R_4$ is methyl or hydrogen and $R_2$ and $R_5$ are hydrogen;

$R_4$ is hydrogen, an alkyl radical containing 1 to 8 carbon atoms, a cycloalkyl radical containing 3 to 6 carbon atoms, a t-alkyl radical containing 4 to 8 carbon atoms, methoxy, phenyl, halogen or methoxycarbonyl, when $R_2$ is hydrogen, an alkyl radical containing 1 to 8 carbon atoms, a cycloalkyl radical containing 3 to 6 carbon atoms and a t-alkyl radical containing 4 to 8 carbon atoms, and $R_3$ and $R_5$ are hydrogen;

$R_5$ is methyl when $R_2$, $R_3$ and $R_4$ are hydrogen, or when $R_4$ is methyl and $R_2$ and $R_3$ are hydrogen, and hydrogen when $R_2$, $R_3$, $R_4$ are the same as above; and when $R_4$ and $R_5$ are (—CH=$CR_7$—CH=CH—), $R_7$ is hydrogen or t-butyl, and $R_2$ is t-butyl or hydrogen and $R_3$ is hydrogen; and when $R_2$ and $R_3$ are (—CH=CH—)$_2$, $R_4$ and $R_5$ are hydrogen.

A preferred group of compounds is obtained when $R_1$ is hydrogen, a 1°, 2° or 3° alkyl group of 1 to 4 carbon atoms, and the —$CH_2CH_2COOR_6$ group where $R_6$ is an alkyl group of 1 to 4 carbon atoms; $R_2$ is hydrogen or a 1°, 2°, or 3° alkyl group of 1 to 4 carbon atoms; $R_3$ is hydrogen or methyl; $R_4$ is hydrogen or a 1°, 2°, or 3° alkyl group of 1 to 4 carbon atoms; and $R_5$ is hydrogen.

A more preferred group of compounds is obtained when $R_1$ is H, $CH_3$, t-butyl, and —$CH_2CH_2COOR_6$; $R_2$ is H, $CH_3$, t-butyl; $R_3$ is H or $CH_3$; $R_4$ is H, $CH_3$ or t-butyl; and $R_5$ is H.

Typical compounds include 2-[4-methyl-2,6-bis(1,1-dimethylethyl)phenoxy]-5,7-bis(1,1-dimethylethyl)-2,3-dihydro-1,2-benzoxaphosphole 2-oxide; 2-[4-methyl-2,6-bis(1,1-dimethylethyl)phenoxy]-2,3-dihydro-1,2-benzoxaphosphole 2-oxide; 2-[4-methyl-2,6-bis(1,1-dimethylethyl)phenoxy]-5-methyl-2,3-dihydro-1,2-benzoxaphosphole 2-oxide; 2-[4-methyl-2,6-bis(1,1-dimethylethyl)phenoxy]-5,7-dimethyl-2,3-dihydro-1,2-benzoxaphosphole 2-oxide; 2-[4-methyl-2,6-bis(1,1-dimethylethyl)phenoxy]-7-(1,1-dimethylethyl)-2,3-dihydro-1,2-benzoxaphosphole 2-oxide; 2-[4-methyl-2,6-bis(1,1-dimethylethyl)phenoxy]-5-(1,1-dimethylethyl)-7-methyl-2,3-dihydro-1,2-benzoxaphosphole 2-oxide; 2-[4-methyl-2,6-bis(1,1-dimethylethyl)phenoxy]-5-methyl-7-(1,1-dimethylethyl)-2,3-dihydro-1,2-benzoxaphosphole 2oxide; 2-[2,4,6-tris(1,1-dimethylethyl)phenoxy]-5,7-bis(1,1-dimethylethyl)-2,3-dihydro-1,2-benzoxaphosphole 2-oxide; 2-[2,4,6-tris(1,1-dimethylethyl)phenoxy]-2,3-dihydro-1,2-benzoxaphosphole 2-oxide; 2-[2,4,6-tris(1,1-dimethylethyl)phenoxy]-5-methyl-2,3-dihydro-1,2-benzoxaphosphole 2oxide; 2-[2,4,6-tris(1,1-dimethylethyl)phenoxy]-5,7-dimethyl-2,3-dihydro-1,2-benzoxaphosphole 2-oxide; 2-[2,4,6-tris(1,1-dimethylethyl)phenoxy]-7-(1,1-dimethylethyl)-2,3-dihydro-1,2-benzoxaphosphole 2-oxide; 2-[2,4,6-tris(1,1-dimethylethyl)phenoxy]-7-(1,1-dimethylethyl)-2,3-dihydro-1,2-benzoxaphosphole 2-oxide; 2-[2,4,6-tris(1,1-dimethylethyl)phenoxy]-5-(1,1-dimethylethyl)-7-methyl-2,3-dihydro-1,2-benzoxaphosphole 2-oxide; and the like.

The cyclic phosphonates of this invention are the reaction products of hindered phenols, ortho-methylolphenols and phosphorous trichloride, to form a family of substituted 2-[alkyl phenoxy]-2,3-dihydro-1,2-benzoxaphosphole 2-oxides.

The ortho-methylolphenols have the general formula

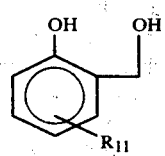

wherein $R_{11}$ may be 1 to 4 hydrogen or alkyl groups containing 1 to 12, preferably 1 to 8 carbon atoms. The preparation of these materials is reported in the literature, and may be made for example by reacting phenols such as p-cresol and 2,4-dimethylphenol with aqueous formaldehyde in caustic solution. Another procedure is to conduct the reaction of the phenol and para formaldehyde with boric acid in solution. Typical ortho-methylolphenols are 2,4-dimethyl-6-hydroxymethylphenol, 2,4-di-t-butyl-6-hydroxymethylphenol, and the like.

The hindered phenols have the general formula

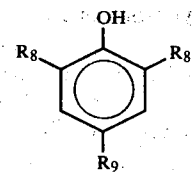

wherein $R_8$ is t-alkyl groups containing from 4 to 12 carbon atoms, but preferably are t-butyl, and $R_9$ is hydrogen, t-alkyl as defined, or alkyl radical containing 1 to 8 carbon atoms, or an ester group, $COOR_{10}$ wherein $R_{10}$ is an alkyl group containing 1 to 8 carbon atoms, and a $CH_2CH_2COOR_6$ group where $R_6$ contains 1 to 8 carbon atoms; such as 2,4,6-tri-t-butylphenol, 2,6-di-t-butyl-4-methylphenol, and the like.

The cyclic phosphonates may be prepared by first reacting the o-methylolphenol with the hindered phenol using phosphorous trichloride and a trialkylamine as a catalyst. A preferred method for preparing the cyclic phosphonates is to react the o-methylolphenol and an alkylphenyl phosphorodichloridite, in an organic solvent in the presence of the trialkylamine catalyst. This results in cyclic phosphites, substituted 2-(2,6-di-t-butyl-4-alkylphenoxy)-4H-1,3,2-benzodioxaphosphorins that are heated to form the cyclic phosphonate. The cyclic phosphonates are isolated from the reaction mixture by distillation for example, but in any event, the reaction product must be heated to a temperature greater than 75° C., preferably 100° C. to about 300° C., or below the decomposition temperature, to cause an intramolecular rearrangement of the phosphite to a phosphonate. The heating is preferably under vacuum and for at least about 30 minutes or more to form the phosphonate rearrangement product. The heating may be in the latter stages of the first reaction to form the phosphonate, after the reaction, after solvent purification of the reaction product, as part of the purification step to remove volatiles as by distillation, and the like. Typical preparations of the o-methylolphenols and cyclic phosphonates therefrom are set forth in the following examples.

2,4-Dimethyl-6-hydroxymethylphenol

A 38% solution of formaldehyde (32.0 grams, 0.4 mol) was added to a stirred solution of 2,4-dimethylphenol (36.6 grams, 0.3 mol) in water (100 ml) containing sodium hydroxide (14 gr., 0.35 mol) and heated at 50° C. for 4 to 5 hours. The reaction was cooled and solid sodium hydroxide added to precipitate the salt of the product. The solid was removed by filtration and dissolved in water. This solution was neutralized with carbon dioxide (dry ice) and the resulting mixture was extracted with methylene chloride. The organic layer was removed, dried, and evaporated to yield a light brown solid. This solid was washed in hexane containing a small amount of toluene to afford a tan solid. The NMR[1] and FD/MS[2] data support the structure 1. Nuclear Magnetic Resonance
2. Field Desorption/Mass Spectrometer 2,4-Di-t-butyl-6-hydroxymethylphenol 2,4-Di-t-butylphenol (20.63 gr., 0.1 mole), paraformaldehyde (3.0 gr., 0.1 mol), boric acid (6.18 g., 0.1 mol) and toluene (50 ml.) were charged into a flask and heated at 80° C. under nitrogen for 48 hours. The mixture was filtered and the solvent removed to provide a brown oil. This oil was dissolved in ether and stirred with an equal volume of 1 N HCl for 2 hours. The ether layer was removed, washed with water, dried (MgSO4) and evaporated to form a soft yellow solid. This solid was stirred in pentane and then filtered to afford a white solid with a melting point of 97°–99° C. The structure was confirmed by NMR and FD/MS.

2-(2,6-di-t-butyl-4-methylphenoxy)-5,7-dimethyl-2,3-dihydro-1,2-benzoxaphosphole 2-oxide 2,4-dimethyl-6-hydroxymethylphenol (7 g., 0.046 mol) was dissolved in dry THF (75 ml.) and cooled to 0° C. Under nitrogen, 2,6-di-t-butyl-4-methylphenylphosphorodichloridite (14.9 g., 0.046 mol) was added to the solution. Triethylamine (9.4 g., 0.093 mol) was added dropwise to the cooled stirred solution. After 3.5 hours, the reaction mixture was filtered and the filtrate was evaporated to dryness to form an off-white friable glass. The glass was stirred in acetonitrile for 2 hours to obtain a white solid, melting point of 132°–138° C.

This product 2-(2,6-di-t-butyl-4-methylphenoxy)-6,8-dimethyl-4H-1,3,2-benzodioxaphosphorin was heated at 150° C. for 2 hours under vacuum to provide an orange glass, melting point 75°–98° C. The 'HNMR supported the structure 2-(2,6-di-t-butyl-4-methylphenoxy)-5,7-dimethyl-2,3-dihydro-1,2-benzoxaphosphole 2-oxide.

The following listed cyclic phosphonates were prepared as described above, except as indicated:

2-[4-methyl-2,6-bis(1,1-dimethylethyl)phenoxy]-5,7-bis(1,1-dimethylethyl)-2,3-dihydro-1,2-benzoxaphosphole 2-oxide, melting point 208°–211° C., molecular weight 484; prepared from 2,4-di-t-butyl-6-hydroxymethylphenol and 2,6-di-t-butyl-4-methylphenylphosophorodichloridite. After completion of the reaction, the cyclic phosphite reaction product was heated to 150° C. at 1.5–1.8 mm pressure for about 1 hour. The volatiles were removed at a 105° C. head temperature. The residue was dissolved in toluene, filtered and heated to evaporate the toluene. The resulting glassy material was stirred in acetonitrile and filtered, to provide a white solid. The same procedure was used in the following preparations, except where indicated.

2-[4-methyl-2,6-bis(1,1-dimethylethyl)phenoxy]-2,3-dihydro-1,2-benzoxaphosphole 2-oxide, melting point 150°–180° C., molecular weight 372; the reaction product was heated to 185° C. at 0.25 mm. The volatiles were removed at 122° C.

2-[4-methyl-2,6-bis(1,1-dimethylethyl)phenoxy]-7-(1,1-dimethylethyl)-2,3-dihydro-1,2-benzoxaphosphole 2-oxide, molecular weight 428; prepared from 2-t-butyl-6-hydroxymethylphenol and 2,6-di-t-butyl-4-methylphenylphosphorodichloridite. The reaction product was heated to 170° C. at 1.6 mm. The product was an orange glass before purification.

2-[4-methyl-2,6-bis(1,1-dimethylethyl)phenoxy]-5-(1,1-dimethylethyl)-7-methyl-2,3-dihydro-1,2-benzoxaphosphole 2-oxide, molecular weight 442; prepared from 4-t-butyl-2-methyl-6-hydroxymethylphenol and 2,6-di-t-butyl-4-methylphenylphosphorodichloridite. The reaction product was heated to 170° C. at 1.5 mm. The resulting heated product was a glass, before washing.

2-[4-methyl-2,6-bis(1,1-dimethylethyl)phenoxy]-5-methyl-7-(1,1-dimethylethyl)-2,3-dihydro-1,2-benzoxaphosphole 2-oxide, molecular weight 442; prepared from 4-methyl-2-t-butyl-6-hydroxymethylphenol and 2,6-di-t-butyl-4-methylphenylphosphorodichloridite. The product was heated to 210° C. at 1.4 mm and the volatiles were stipped off at 85°-130° C. The resulting residue was a glass before purification.

2-[2,4,6-tris(1,1-dimethylethyl)phenoxy]-5-methyl-2,3-dihydro-1,2-benzoxaphosphole 2-oxide, molecular weight 428; prepared from 4-methyl-2-hydroxymethylphenol and 2,4,6-tri-t-butylphenylphosphorodichloridite. The product was heated to 170° C. at 1.5 mm. The residue was an orange glass before purification.

2-[2,4,6-tris(1,1-dimethylethyl)phenoxy]-5-(1,1-dimethylethyl)-7-methyl-2,3-dihydro-1,2-benzoxaphosphole 2-oxide, melting point 252°-255° C. and molecular weight 486; the reaction product was heated to 185° C. at 1.8 mm. The residue was glassy and was washed in methanol.

The structure and molecular weight of all the above cyclic phosphonates were determined or confirmed by Nuclear Magnetic Resonance, Infra-red and FD/MS.

The hydroxyphenylalkyleneyl isocyanurate compounds used in combination with the cyclic phosphites of this invention have the formula

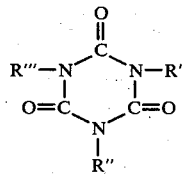

wherein R' is a hydroxyphenylalkyleneyl radical of the formula

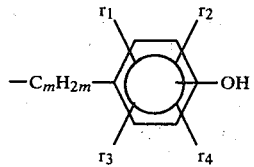

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R" and R"' are hydrogen, an alkyl radical containing 1 to 18 carbon atoms, or are the same as r'. A more preferred compound is when R" and R"' are equal to R', i.e., all the R groups are hydroxyphenylalkyleneyl radicals, and $r_1$ is a t-alkyl radical containing from 4 to about 12 carbon atoms, $r_2$ is a t-alkyl radical containing from 1 to about 12 carbon atoms, $r_3$ and $r_4$ are hydrogen, and m=1.

Even more preferred are the symmetrical tris(3,5-di-t-ert-alkyl-4-hydroxybenzyl)isocyanurates of the formula

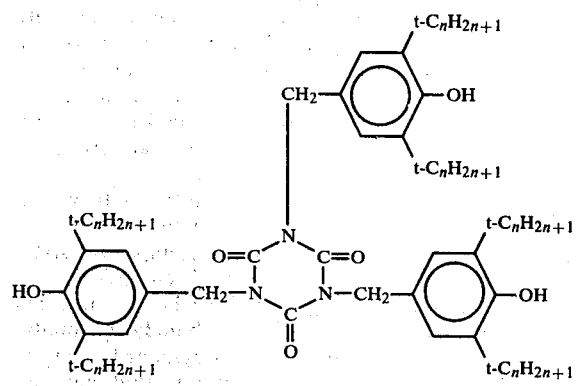

where n is 4 to 8.

Examples of the 4-hydroxybenzyl isocyanurate compounds are: tris-3-t-butyl-4-hydroxybenzyl)isocyanurate, tris-(3-cetyl-4-hydroxybenzyl)isocyanurate, tris(3,5-dimethyl-4-hydroxybenzyl)isocyanurate, tris-(3-methyl-5-isopropyl-4-hydroxybenzyl)isocyanurate, tris(3,5-di-t-butyl-4-hydroxybenzyl)isocyanurate, tris-(3-t-butyl-5-t-amyl-4-hydroxybenzyl)isocyanurate, tris-[3,5-di-(1-methyl-1-ethylpropyl)4-hydroxybenzyl]isocyanurate, tris-[3,5-di-(1,1,2,2-tetramethylpropyl)-4-hydroxybenzyl]isocyanurate, bis-(3,5-dimethyl-4-hydroxybenzyl)isocyanurate, (3-methyl-4-hydroxybenzyl)isocyanurate, (3-t-butyl-4-hydroxybenzyl)isocyanurate, and the like. Reference is made to U.S. Pat. No. 3,531,483 which discloses isocyanurate compounds encompassed by this invention. The disclosure of this patent is incorporated herein by reference.

The amount of cyclic phosphonate used may vary from about 0.01 to 10 weight parts per 100 weights parts of material to be stabilized. More usually about 0.1 to 4.0 parts are used for mixtures with the hydroxyphenylalkyleneyl isocyanurate. The hydroxyphenylalkyleneyl isocyanurate compound is used at a level from about 0.01 part to about 5 parts by weight, and more preferably at from about 0.05 part to about 3 parts by weight per 100 parts by weight of the organic material. The cyclic phosphonate compound is employed at similar levels, i.e., from about 0.01 part to 5 parts and preferably at about 0.05 part to about 3 parts by weight per 100 parts by weight of organic material. Thus the combined weight of the compounds is normally from about 0.02 part to about 10 parts and more preferably from about 0.1 to 6 parts by weight per 100 parts by weight of organic material. The hydroxyphenylalkyleneyl isocyanurate can be used in from about 10:1 to 1:10 weight ratio of isocyanurate compound to cyclic phosphonate compound. Excellent results are obtained at about a 3:1 to 1:3 weight ratio. A 1:1 weight ratio of the compounds provides effective stabilization of organic materials.

Both the cyclic phosphonate and the combinations with the isocyanurate compound and the cyclic phosphonate compound as defined herein provide exceptional heat stability to polyolefin polymers. The combination is especially useful for the stabilization of α-monoolefin homopolymers and copolymers, wherein the α-monoolefin contains 2 to about 8 carbon atoms. High and low-density polyethylene, isotactic and atactic polypropylene, polyisobutylene, and poly(4-methyl-1-pentene) have excellent resistance to ultra violet light when stabilized with the combinations of the present invention. Ethylene-propylene (EP) copolymers and ethylene-propylene (EPDM) terpolymers generally containing less than about 10 percent by weight of one or more monomers containing multiple unsaturation provided, for example, by 1,4-hexadiene, dimethyl-1,4,9-decatriene, dicyclopentadiene, vinyl norbornene, ethylidene norbornene and the like also are stabilized using the combination.

Other organic materials which can be stabilized in accordance with the present invention include both natural and synthetic polymers. For example, the stabilizers are useful for the stabilization of cellulosic materials; natural rubber, halogenated rubber, conjugated diene polymers, as, for instance, polybutadiene, copolymers of butadiene with styrene, acrylonitrile, acrylic acid alkyl acrylates or methacrylates, methyl vinyl ketone, vinyl pyridine, etc.; polyisoprene, polychloroprene, and the like; vinyl polymers such as polyvinyl chloride, polyvinylidene chloride, copolymers of vinyl chloride with vinylidene chloride, polyvinyl acetate, copolymers or vinyl halide with butadiene, styrene, vinyl esters, α,β-unsaturated ketones and aldehydes, and the like; homopolymers and copolymers of acrylic monomers such as methyl acrylate, methyl methacrylate, ethyl acrylate, 3-ethylhexyl acrylate, acrylamide, methacrylamide, N-methylol-acrylamide, acrylonitrile, methacrylonitrile, and the like; epihalohydrin polymers; polyether- or polyol-derived polyurethanes; acetal homo-polymers and copolymers; polycarbonates; polyesters such as those derived from maleic, fumaric, itaconic, or terephthalic anhydrides, or the like; for example, polyethylene terephthalate; polyamides such as those derived from the reaction of hexa-methylenediamine with adipic or sebacic acid; epoxy resins such as those obtained from the condensation of epichlorohydrin with bisphenols; ring opened olefin polymers and the like. Polymer blends, that is, physical admixture of two or more polymers may also be stabilized in accordance with the present invention.

In addition to polymeric materials, the present compounds may stabilize a wide variety of other organic materials. Such compounds include: waxes, synthetic and petroleum-derived lubricating oils and greases; animal oils such as, for example, fat, tallow, lard, cod-liver oil, sperm oil; vegetable oils such as castor, linseed, peanut, palm, cotton seed, and the like; fuel oil; diesel oil, gasoline, and the like.

The compounds are readily incorporated into materials by dissolving or dispersing them with the materials or in liquid, dispersion solutions and solid forms. If the material is a solid, especially a polymeric solid such as a rubber or a plastic, the compounds can be admixed using internal mixers as Banburys, extruders, two-roll mills, and the like, following conventional techniques. One way to disperse the compounds in plastic materials is to dissolve or suspend the compounds in a solvent, mix the mixture with a plastic in powder or solution form, and then evaporate the solvent.

Compositions containing the novel combination of compounds can also contain other known compounding ingredients such as fillers like carbon black, silica, metal carbonates, talc, asbestos, and the like; pigments and colorants; curative ingredients like sulfur and peroxides and vulcanization accelerators; fungicides; processing aids, reinforcing agents and standard ingredients known to the art. Other ingredients known in the art as ultra-violet light, thermal and/or oxidative stabilizers can also be used in the stabilized compositions.

Test samples were prepared by mixing the stabilizer compounds with polypropylene in a Brabender Plasticorder fitted with a Cam-Head (mixing chamber). The polypropylene is first masticated for 1½ minutes at 190° C. Then the stabilizer mixture is added, following by 3 minutes additional mixing. The mass is removed and pressed into 20 mil thick sheets. From these sheets are cut 1"×1" plaques for oven-aging. Type C (3"×⅜") tensil bars are cut for UV stability tests.

Thermal/oxidative stability (oven-aging) testing consisted of aging the samples in triplicate in an air-circulating oven at 125° C. The time to catastrophic crumbling (failure) of the plaque is measured and reported as days to failure.

Each sample contained 0.1 weight part of cyclic phosphonate per 100 weight parts of polypropylene. The following results were obtained:

2-[4-methyl-2,6-bis(1,1-dimethylethyl)phenoxy]-2,3-dihydro-1,2-benzoxaphosphole 2-oxide, 6⅓ days;

2-[4-methyl-2,6-bis(1,1-dimethylethyl)phenoxy]-7-(1,1-dimethylethyl)-2,3-dihydro-1,2-benzoxaphosphole 2-oxide, 7 days;

2-[4-methyl-2,6-bis(1,1-dimethylethyl)phenoxy]-5-(1,1-dimethylethyl)-7-methyl-2,3-dihydro-1,2-benzoxaphosphole 2-oxide, 6 ⅓ days;

2-[4-methyl-2,6-bis(1,1-dimethylethyl)phenoxy]-5-methyl-7-(1,1-dimethylethyl)-2,3-dihydro-1,2-benzoxaphosphole 2-oxide, 7 days;

2-[2,4,6-tris(1,1-dimethylethyl)phenoxy]-5-methyl-2,3-dihydro-1,2-benzoxaphosphole 2-oxide, 4 days.

To demonstrate the unexpected synergistic enhancement of anti-oxidant activity when the cyclic phosphonates of this invention are combined with a hydroxyphenylalkyleneyl isocyanurate, test samples of polypropylene with 0.05 weight part each of tris(3,5-di-t-butyl-4-hydroxy-benzyl)isocyanurate and the cyclic phosphonates listed below were prepared and tested in the air oven until failure. The results obtained were as follows:

2-[4-methyl-2,6-bis(1,1-dimethylethyl)phenoxy]-7-(1,1-dimethylethyl)-2,3-dihydro-1,2-benzoxaphosphole 2-oxide, 36⅔ days;

2-[4-methyl-2,6-bis(1,1-dimethylethyl)phenoxy]-5-(1,1-dimethylethyl)-7-methyl-2,3-dihydro-1,2-benzoxaphosphole 2-oxide, 42⅓ days;

2-[4-methyl-2,6-bis(1,1-dimethylethyl)phenoxy]-5-methyl-7-(1,1-dimethylethyl)-2,3-dihydro-1,2-benzoxaphosphole 2-oxide, 36 days;

2-[2,4,6-tris(1,1-dimethylethyl)phenoxy]-5-methyl-2,3-dihydro-1,2-benzoxaphosphole 2-oxide, 37 days.

These values are better than those obtained with many commercially available cyclic stabilizers in the same compositions. For example, when these tests are repeated with tris(2,4-di-t-butylphenyl)phosphite, a value of only 17⅔ days was observed.

I claim:

1. 2-[alkylphenoxy]-2,3-dihydro-1,2-benzoxaphosphole 2-oxide cyclic phosphonates of the formula:

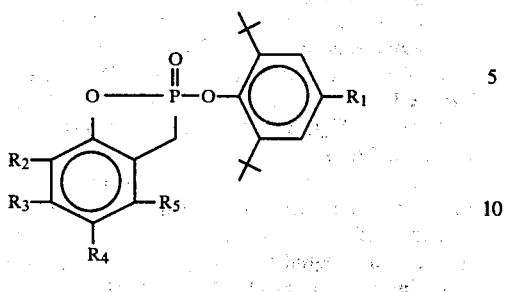

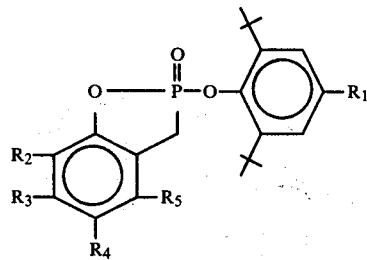

wherein:

✝ is t-butyl; $R_1$ is hydrogen, an alkyl radical containing 1 to 8 carbon atoms, a cycloalkyl radical containing 3 to 6 carbon atoms, halogen, an alkoxy radical containing 1 to 8 carbon atoms, phenyl, a —$CH_2CH_2COOR_6$ group wherein $R_6$ is an alkyl radical containing 1 to 8 carbon atoms, or a t-alkyl radical containing 4 to 8 carbon atoms; $R_2$ is hydrogen, an alkyl radical containing 1 to 8 carbon atoms, and methoxy or phenyl when $R_3$, $R_4$ and $R_5$ are hydrogen, or when $R_3$ and $R_4$ are hydrogen and $R_5$ is methyl; $R_3$ is methyl when $R_4$ is methyl or hydrogen and $R_2$ and $R_5$ are hydrogen; $R_4$ is hydrogen, an alkyl radical containing 1 to 8 carbon atoms, a cycloalkyl radical containing 3 to 6 carbon atoms, a t-alkyl radical containing 4 to 8 carbon atoms, methoxy, phenyl, halogen or methoxycarbonyl, when $R_2$ is hydrogen, an alkyl radical containing 1 to 8 carbon atoms, a cycloalkyl radical containing 3 to 6 carbon atoms and a t-alkyl radical containing 4 to 8 carbon atoms, and $R_3$ and $R_5$ are hydrogen; $R_5$ is methyl when $R_2$, $R_3$ and $R_4$ are hydrogen, or when $R_4$ is methyl and $R_2$ and $R_3$ are hydrogen, and hydrogen when $R_2$, $R_3$, $R_4$ are the same as above; and when $R_4$ and $R_5$ are (—CH=CH₇—CH=CH—), $R_7$ is hydrogen or t-butyl, and $R_2$ is t-butyl or hydrogen and $R_3$ is hydrogen; and when $R_2$ and $R_3$ are (—CH=CH—)$_2$, $R_4$ and $R_5$ are hydrogen.

2. Cyclic phosphonates of claim 1 wherein $R_1$ is hydrogen, a 1°, 2° or 3° alkyl group of 1 to 4 carbon atoms, and the —$CH_2CH_2COOR_6$ group where $R_6$ is an alkyl group of 1 to 4 carbon atoms; $R_2$ is hydrogen or a 1°, 2°, or 3° alkyl group of 1 to 4 carbon atoms; $R_3$ is hydrogen or methyl; $R_4$ is hydrogen or a 1°, 2°, or 3° alkyl group of 1 to 4 carbon atoms; and $R_5$ is hydrogen.

3. A cyclic phosphonate of claim 2, 2-[4-methyl-2,6-bis(1,1-dimethylethyl)phenoxy]-7-(1,1-dimethylethyl)-2,3-dihydro-1,2-benzophosphole 2-oxide.

4. A cyclic phosphonate of claim 2, 2-[4-methyl-2,6-bis(1,1-dimethylethyl)phenoxy]-5-(1,1-dimethylethyl)-7-methyl-2,3-dihydro-1,2-benzoxaphosphole 2-oxide.

5. A cyclic phosphonate of claim 2, 2-[4-methyl-2,6-bis(1,1-dimethylethyl)phenoxy]-5-methyl-7-(1,1-dimethylethyl)-2,3-dihydro-1,2-benzoxaphosphole 2-oxide.

6. A cyclic phosphonate of claim 2, 2-[2,4,6-tris(1,1-dimethylethyl)phenoxy]-5-methyl-2,3-dihydro-1,2-benzoxaphosphole 2-oxide.

7. A composition comprising organic materials subject to degradation and stabilizing amounts of 2-[alkylphenoxy]-2,3-dihydro-1,2-benzoxaphosphole 2-oxide cyclic phosphonates of the formula:

8. A composition of claim 7 wherein said organic material is a polymer and $R_1$ is hydrogen, a 1°, 2°, or 3° alkyl group of 1 to 4 carbon atoms, and the —$CH_2CH_2COOR_6$ group where $R_6$ is an alkyl group of 1 to 4 carbon atoms; $R_2$ is hydrogen or a 1°, 2°, or 3° alkyl group of 1 to 4 carbon atoms; $R_3$ is hydrogen or methyl; $R_4$ is hydrogen or a 1°, 2°, or 3° alkyl group of 1 to 4 carbon atoms; and $R_5$ is hydrogen.

9. A composition of claim 8 containing a polyolefin and 2-[4-methyl-2,6-bis(1,1-dimethylethyl)phenoxy]-7-(1,1-dimethylethyl)-2,3-dihydro-1,2-benzoxaphosphole 2-oxide.

10. A composition of claim 8 containing a polyolefin and 2-[4-methyl-2,6-bis(1,1-dimethylethyl)phenoxy]-5-(1,1-dimethylethyl)-7-methyl-2,3-dihydro-1,2-benzoxaphosphole 2-oxide.

11. A composition of claim 8 containing a polyolefin and 2-[4-methyl-2,6-bis(1,1-dimethylethyl)phenoxy]-5-methyl-7-(1,1-dimethylethyl)-2,3-dihydro-1,2-benzoxaphosphole 2-oxide.

12. A composition of claim 8 containing a polyolefin and 2-[2,4,6-tris(1,1-dimethylethyl)phenoxy]-5-methyl-2,3-dihydro-1,2-benzoxaphosphole 2-oxide.

13. A stabilizer composition for organic materials subject to degradation comprising (1) 2-[alkylphenoxy]-

2,3-dihydro-1,2-benzoxaphosphole 2-oxide cyclic phosphonates of the formula:

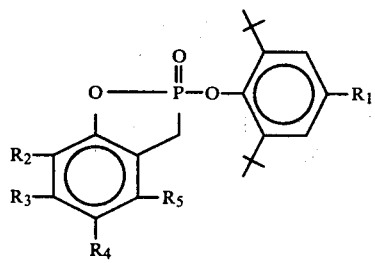

wherein:

$\dagger$ is t-butyl; $R_1$ is hydrogen, an alkyl radical containing 1 to 8 carbon atoms, a cycloalkyl radical containing 3 to 6 carbon atoms, halogen, an alkoxy radical containing 1 to 8 carbon atoms, phenyl, a $-CH_2CH_2COOR_6$ group wherein $R_6$ is an alkyl radical containing 1 to 8 carbon atoms, or a t-alkyl radical containing 4 to 8 carbon atoms; $R_2$ is hydrogen, an alkyl radical containing 1 to 8 carbon atoms, and methoxy or phenyl when $R_3$, $R_4$ and $R_5$ are hydrogen, or when $R_3$ and $R_4$ are hydrogen and $R_5$ is methyl; $R_3$ is methyl when $R_4$ is methyl or hydrogen and $R_2$ and $R_5$ are hydrogen; $R_4$ is hydrogen, an alkyl radical containing 1 to 8 carbon atoms, a cycloalkyl radical containing 3 to 6 carbon atoms, a t-alkyl radical containing 4 to 8 carbon atoms, methoxy, phenyl, halogen or methoxycarbonyl, when $R_2$ is hydrogen, an alkyl radical containing 1 to 8 carbon atoms, a cycloalkyl radical containing 3 to 6 carbon atoms and a t-alkyl radical containing 1 to 8 carbon atoms, and $R_3$ and $R_5$ are hydrogen; $R_5$ is methyl when $R_2$, $R_3$ and $R_4$ are hydrogen, or when $R_4$ is methyl and $R_2$ and $R_3$ are hydrogen, and hydrogen when $R_2$, $R_3$, $R_4$ are the same as above; and when $R_4$ and $R_5$ are (—CH=C-$R_7$—CH=CH—), $R_7$ is hydrogen or t-butyl, and $R_2$ is t-butyl or hydrogen and $R_3$ is hydrogen; and when $R_2$ and $R_3$ are (—CH=CH—)$_2$, $R_4$ and $R_5$ are hydrogen, and (2) a hydroxyphenylalkyleneyl isocyanurate of the formula

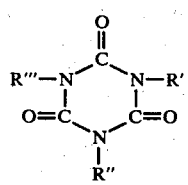

wherein R' is a hydroxyphenylalkyleneyl radical of the formula

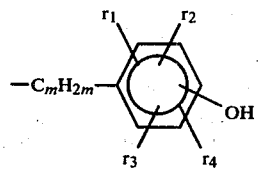

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R" and R'" are hydrogen, an alkyl radical containing 1 to 18 carbon atoms, or are the same as r'. A more preferred compound is when R" and R'" are equal to R'.

14. A stabilizer of claim 13 wherein in (1) $R_1$ is hydrogen, a 1°, 2° or 3° alkyl group of 1 to 4 carbon atoms, and the —CH$_2$CH$_2$COOR$_6$ group where $R_6$ is an alkyl group of 1 to 4 carbon atoms; $R_2$ is hydrogen or a 1°, 2°, or 3° alkyl group of 1 to 4 carbon atoms; $R_3$ is hydrogen or methyl; $R_4$ is hydrogen or a 1°, 2° or 3° alkyl group of 1 to 4 carbon atoms; and $R_5$ is hydrogen; and in (2) R" and R'" are equal to R', $r_1$ is a tertiary alkyl radical containing 4 to about 12 carbon atoms, $r_2$ is an alkyl radical containing 1 to about 12 carbon atoms, $r_3$ and $r_4$ are hydrogen, and m=1.

15. A stabilizer of claim 14 where (2) has the formula

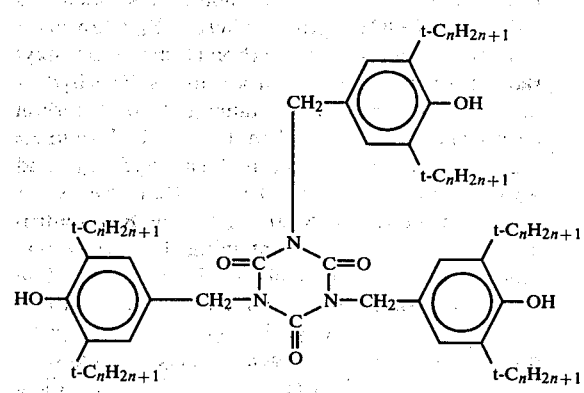

where n is 4 to 8.

16. A stabilizer of claim 15 where (2) is 1,3,5-tris(3,5-di-t-butyl-4-hydroxybenzyl) isocyanurate.

17. A stabilizer of claim 16 wherein (1) is 2-[4-methyl-2,6-bis(1,1-dimethylethyl)phenoxy]-7-(1,1-dimethylethyl)-2,3-dihydro-1,2-benzoxaphosphole 2-oxide.

18. A stabilizer of claim 16 wherein (1) is 2-[4-methyl-2,6-bis(1,1-dimethylethyl)phenoxy]-5-(1,1-dimethylethyl)-7-methyl-2,3-dihydro-1,2-benzoxaphosphole 2-oxide.

19. A stabilizer of claim 16 wherein (1) is 2-[4-methyl-2,6-bis(1,1-dimethylethyl)phenoxy]-5-methyl-7-(1,1-dimethylethyl)-2,3-dihydro-1,2-benzoxaphosphole 2-oxide.

20. A stabilizer of claim 16 wherein (1) is 2-[2,4,6-tris(1,1-dimethylethyl)phenoxy]-5-methyl-2,3-dihydro-1,2-benzoxaphosphole 2-oxide.

21. A composition comprising organic materials subject to degradation and stabilizing amounts of (1) 2-[alkylphenoxy]-2,3-dihydro-1,2-benzoxaphosphole 2-oxide cyclic phosphonates of the formula:

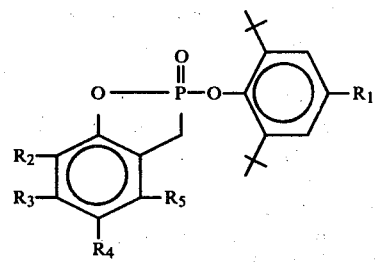

wherein:

✝ is t-butyl; $R_1$ is hydrogen, an alkyl radical containing 1 to 8 carbon atoms, a cycloalkyl radical containing 3 to 6 carbon atoms, halogen, an alkoxy radical containing 1 to 8 carbon atoms, phenyl, a —$CH_2CH_2COOR_6$ group wherein $R_6$ is an alkyl radical containing 1 to 8 carbon atoms, or a t-alkyl radical containing 4 to 8 carbon atoms; $R_2$ is hydrogen, an alkyl radical containing 1 to 8 carbon atoms, and methoxy or phenyl when $R_3$, $R_4$ and $R_5$ are hydrogen, or when $R_3$ and $R_4$ are hydrogen and $R_5$ is methyl; $R_3$ is methyl when $R_4$ is methyl or hydrogen and $R_2$ and $R_5$ are hydrogen; $R_4$ is hydrogen, an alkyl radical containing 1 to 8 carbon atoms, a cycloalkyl radical containing 3 to 6 carbon atoms, a t-alkyl radical containing 4 to 8 carbon atoms, methoxy, phenyl, halogen or methoxycarbonyl, when $R_2$ is hydrogen, an alkyl radical containing 1 to 8 carbon atoms, a cycloalkyl radical containing 3 to 6 carbon atoms and a t-alkyl radical containing 4 to 8 carbon atoms, and $R_3$ and $R_5$ are hydrogen; $R_5$ is methyl when $R_2$, $R_3$ and $R_4$ are hydrogen, or when $R_4$ is methyl and $R_2$ and $R_3$ are hydrogen, and hydrogen when $R_2$, $R_3$, $R_4$ are the same as above;

and when $R_4$ and $R_5$ are (—CH=$CR_7$—CH=CH—), $R_7$ is hydrogen or t-butyl, and $R_2$ is t-butyl or hydrogen and $R_3$ is hydrogen; and when $R_2$ and $R_3$ are (—CH=CH—)$_2$, $R_4$ and $R_5$ are hydrogen, and (2) a hydroxyphenylalkyleneyl isocyanurate of the formula

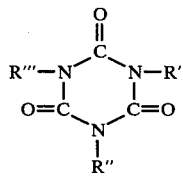

wherein R' is a hydroxyphenylalkyleneyl radical of the formula

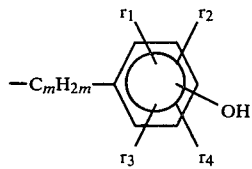

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R" and R''' are hydrogen, an alkyl radical containing 1 to 18 carbon atoms, or are the same as R'.

22. A composition of claim 21 wherein said organic material is a polymer and in (1) $R_1$ is hydrogen, a 1°, 2° or 3° alkyl group of 1 to 4 carbon atoms, and the —$CH_2CH_2COOR_6$ group where $R_6$ is an alkyl group of 1 to 4 carbon atoms; $R_2$ is hydrogen or a 1°, 2°, or 3° alkyl group of 1 to 4 carbon atoms; $R_3$ is hydrogen or methyl; $R_4$ is hydrogen or a 1°, 2°, or 3° alkyl group of 1 to 4 carbon atoms; and $R_5$ is hydrogen.

23. A composition of claim 22 wherein in (2) R" and R''' are equal to R', $r_1$ is a tertiary alkyl radical containing 4 to about 12 carbon atoms, $r_2$ is an alkyl radical containing 1 to about 12 carbon atoms, $r_3$ and $r_4$ are hydrogen, and m=1.

24. A composition of claim 23 where (2) has the formula

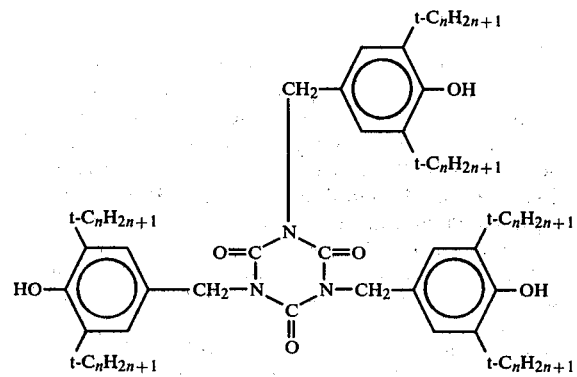

where n is 4 to 8.

25. A composition of claim 24 where (2) is 1,3,5-tris(3,5-di-t-butyl-4-hydroxybenzyl) isocyanurate.

26. A composition of claim 25 wherein said polymer is a polyolefin and (1) is 2-[4-methyl-2,6-bis(1,1-dimethylethyl)phenoxy]-7-(1,1-dimethylethyl)-2,3-dihydro-1,2-benzoxaphosphole 2-oxide.

27. A composition of claim 25 wherein said polymer is a polyolefin and (1) is 2-[4-methyl-2,6-bis(1,1-dimethylethyl)phenoxy]-5-(1,1-dimethylethyl)-7-methyl-2,3-dihydro-1,2-benzoxaphosphole 2-oxide.

28. A composition of claim 25 wherein said polymer is a polyolefin and (1) is 2-[4-methyl-2,6-bis(1,1-dimethylethyl)phenoxy]-5-methyl-7-(1,1-dimethylethyl)-2,3-dihydro-1,2-benzoxaphosphole 2-oxide.

29. A composition of claim 25 wherein said polymer is a polyolefin and (1) is 2-[2,4,6-tris(1,1-dimethylethyl)phenoxy]-5-methyl-2,3-dihydro-1,2-benzoxaphosphole 2-oxide.

* * * * *

UNITED STATES PATENT AND TRADEMARK OFFICE
CERTIFICATE OF CORRECTION

PATENT NO. : 4,439,564
DATED : March 27, 1984
INVENTOR(S) : DWIGHT WILLIAM CHASAR It is certified that error appears in the above-identified patent and that said Letters Patent are hereby corrected as shown below:

Claim 1, column 9, line 40 "$H_7$" should read --$R_7$--;

Claim 3, column 9, line 54 "benzophosphole" should read --benzoxaphosphole--;

Claim 7, line 40 "$H_7$" should read --$R_7$--.

Signed and Sealed this

Thirteenth Day of August 1985

[SEAL]

Attest:

DONALD J. QUIGG

Attesting Officer   Acting Commissioner of Patents and Trademarks